(12) United States Patent
Bachrach et al.

(10) Patent No.: US 11,024,080 B2
(45) Date of Patent: ***Jun. 1, 2021

(54) TECHNIQUES FOR SLICING A 3D MODEL FOR MANUFACTURING

(71) Applicant: AUTODESK, INC., San Rafael, CA (US)

(72) Inventors: Jonathan Bachrach, Berkeley, CA (US); Saul Griffith, San Francisco, CA (US)

(73) Assignee: AUTODESK, INC., San Rafael, CA (US)

( * ) Notice: Subject to any disclaimer, the term of this patent is extended or adjusted under 35 U.S.C. 154(b) by 515 days.

This patent is subject to a terminal disclaimer.

(21) Appl. No.: 13/792,619

(22) Filed: Mar. 11, 2013

(65) Prior Publication Data

US 2014/0253549 A1    Sep. 11, 2014

(51) Int. Cl.
*G06T 19/00*     (2011.01)
*A61F 2/915*    (2013.01)

(52) U.S. Cl.
CPC ............. *G06T 19/00* (2013.01); *A61F 2/915* (2013.01); *G06T 2219/008* (2013.01)

(58) Field of Classification Search
CPC ..... G06F 17/5081; G06T 17/20; G06T 19/00; A61F 2/915
USPC ..................................... 345/420; 700/98–119
See application file for complete search history.

(56) References Cited

U.S. PATENT DOCUMENTS

| 5,137,662 | A | 8/1992 | Hull et al. |
| 5,371,778 | A | 12/1994 | Yanof et al. |
| 5,596,504 | A | 1/1997 | Tata et al. |
| 7,063,532 | B1 | 6/2006 | Jones et al. |
| 8,160,345 | B2 | 4/2012 | Pavlovskaia et al. |
| 8,311,306 | B2 | 11/2012 | Pavlovskaia et al. |
| 8,480,679 | B2 | 7/2013 | Park et al. |
| 8,483,469 | B2 | 7/2013 | Pavlovskaia et al. |
| 8,532,361 | B2 | 9/2013 | Pavlovskaia et al. |
| 8,545,509 | B2 | 10/2013 | Park et al. |
| 8,868,230 | B2 | 10/2014 | Tschanz et al. |
| 2002/0037489 | A1 | 3/2002 | Jones et al. |
| 2002/0126884 | A1 | 9/2002 | Gerritsen et al. |

(Continued)

OTHER PUBLICATIONS

Marsan et al., An Assessment of Data Requirements and Data Transfer Formats for Layered Manufacturing, Sep. 1998, Technical Report NISTIR 6216, National Institute of Standards and Technology (NIST), pp. 1-55.*

(Continued)

*Primary Examiner* — Matthew Salvucci
(74) *Attorney, Agent, or Firm* — Artegis Law Group, LLP

(57) ABSTRACT

One embodiment of the invention is a slicing engine that generates two or more slices of a virtual 3D model given a slice plane. The slicing engine then determines connection points on each of the slices that indicate how the 3D model is to be reconnected by the user when the 3D model is fabricated. The slicing engine also determines an optimized layout for the various slices of the 3D model on fabrication material for minimal use of the material. The user is then able to "print" the layout on the fabrication material via 3D printers, and connect the various printed slices according to the connection points to build a physical representation of the 3D model.

18 Claims, 16 Drawing Sheets

(56) References Cited

U.S. PATENT DOCUMENTS

| | | | |
|---|---|---|---|
| 2004/0222549 A1* | 11/2004 | Sano et al. | 264/128 |
| 2005/0151735 A1 | 7/2005 | Boekhorst | |
| 2006/0155418 A1 | 7/2006 | Bradbury et al. | |
| 2006/0290695 A1 | 12/2006 | Salomie | |
| 2007/0233298 A1 | 10/2007 | Heide et al. | |
| 2009/0174709 A1 | 7/2009 | Kozlak et al. | |
| 2010/0023015 A1 | 1/2010 | Park | |
| 2010/0042105 A1 | 2/2010 | Park et al. | |
| 2010/0132120 A1 | 6/2010 | Koerlin et al. | |
| 2011/0189440 A1 | 8/2011 | Appleby et al. | |
| 2011/0282207 A1 | 11/2011 | Hashimoto | |
| 2012/0245465 A1 | 9/2012 | Hansegard et al. | |
| 2014/0023996 A1* | 1/2014 | Finn | G09B 25/00 434/72 |
| 2014/0253549 A1 | 9/2014 | Bachrach et al. | |
| 2014/0253550 A1 | 9/2014 | Bachrach et al. | |
| 2014/0257547 A1 | 9/2014 | Bachrach et al. | |

OTHER PUBLICATIONS

Non-Final Office Action for U.S. Appl. No. 13/792,789, dated Jul. 1, 2015.
Final Office Action for U.S. Appl. No. 13/792,655, dated May 20, 2015.
Final Office Action received for U.S. Appl. No. 13/792,789, dated Dec. 1, 2015, 28 pages.
Non-Final Office Action received for U.S. Appl. No. 13/792,753 dated Dec. 17, 2015, 26 pages.
Final Office Action received for U.S. Appl. No. 13/792,753 dated Jun. 15, 2016, 13 pages.
Non-Final Office Action received for U.S. Appl. No. 13/792,753 dated Dec. 14, 2016, 8 pages.
Notice of Allowance received for U.S. Appl. No. 13/792,753 dated Apr. 10, 2017, 11 pages.
Non-Final Office Action received for U.S. Appl. No. 13/792,655 dated Jan. 16, 2015, 93 pages.
Non-Final Office Action received for U.S. Appl. No. 13/792,655 dated Sep. 16, 2015, 36 pages.
Final Office Action received for U.S. Appl. No. 13/792,655 dated Feb. 25, 2016, 38 pages.
Non-Final Office Action received for U.S. Appl. No. 13/792,655 dated Aug. 16, 2016, 34 pages.
Final Office Action received for U.S. Appl. No. 13/792,655 dated Nov. 29, 2016, 35 pages.
Notice of Allowance received for U.S. Appl. No. 13/792,655 dated Apr. 27, 2017, 30 pages.
Notice of Allowance received for U.S. Appl. No. 13/792,789, dated Mar. 28, 2018, 15 pages.

* cited by examiner

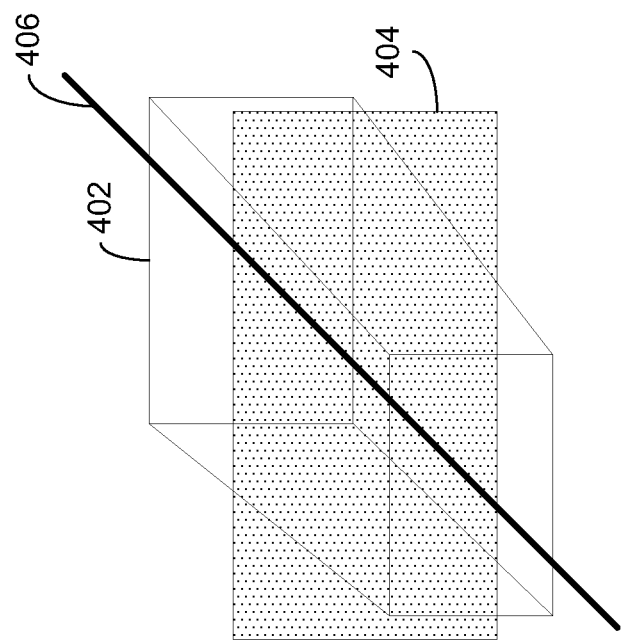

TECHNIQUES FOR SLICING A 3D MODEL FOR MANUFACTURING

BACKGROUND OF THE INVENTION

Field of the Invention

Embodiments presented in this disclosure generally relate to computer aided design (CAD) and computer aided manufacturing (CAM). More specifically, embodiments presented herein provide techniques for slicing 3D models for manufacturing.

Description of the Related Art

CAD/CAM applications provide software modeling tools used to create designs for real-world three-dimensional (3D) objects. For example, a designer may use such a software application to create a 3D model of a constructible toy having a particular shape when inflated. Other examples include 3D computer models of sculpture, furniture, clothing, etc.

Some designers may wish to manufacture a 3D model created in a CAD/CAM application. Typically, to facilitate manufacturing, the CAD/CAM application processes the 3D model to create a blueprint. The designer can then submit the blueprint to a third-party manufacturer for building a physical representation of the 3D model or, alternatively, acquire manufacturing material to build the physical representation according to the blueprint herself.

The blueprint typically describes, only at a high level, the structural aspects of the 3D model, but does not provide any further assistance to the designer regarding how to manufacture the physical representation. Consequently, for 3D models with even a slight amount of complexity, the designer is required to have a manufacturer build the physical representation. Having to resort to a manufacturer in the design phase is typically undesirable for the designer because of two primary factors. First, production costs of building the physical representation increase when the designer involves the manufacturer. Second, the time to build the physical representation is dramatically increased if the designer is required to build the physical representation through a manufacturer. Again, designers who want to produce a quick-to-market item want to avoid delaying the production or the prototyping of the 3D model.

As the foregoing illustrates, what is needed in the art are techniques for designing and building a 3D model that mitigate the cost and delay typically associated with having a third-party manufacturer build the 3D model.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIG. 4 illustrates a slice plane selected by a user for slicing a 3D model of a cuboid, according to one embodiment of the invention.

SUMMARY

Embodiments presented herein provide techniques for generating a real-world three-dimensional (3D) model. The method includes the steps of slicing a 3D graphics model generated by a software application along at least one axis to generate a plurality of slices and determining that a first slice included in the plurality of slices is to be connected to a second slice also included in the plurality of slices. The method also includes the steps of identifying a connection location on each of the first slice and the second slice where the first slice and the second slice are to be connected, and causing an indication of the connection location to be generated on each of the first slice and the second slice when the first slice and the second slice are manufactured.

One advantage of the disclosed techniques is that an end-user is able to build 3D models quickly and without the need of a professional third party manufacturer. More specifically, the slicing engine processes a virtual 3D model in such a manner that, to physically manufacture the 3D model, a user simply prints the layout of the slices generated by the slicing engine onto fabrication material and then connects the slices to build the model.

DETAILED DESCRIPTION

Figure 1:
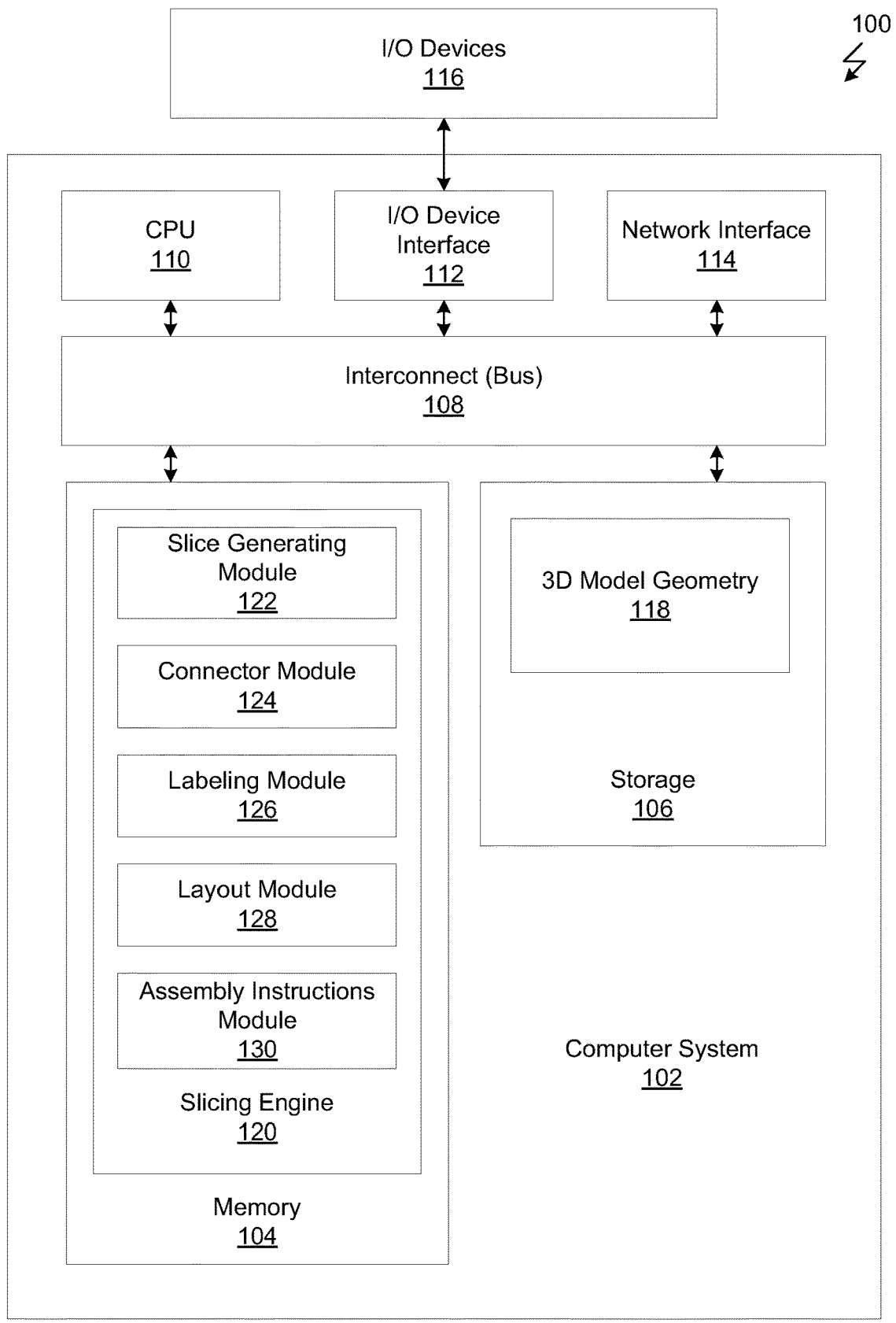
FIG. 1 illustrates an example system 100 configured to slice a 3D model and prepare the sliced model for manufacturing, according to one embodiment of the invention.

FIG. 1 illustrates an example system 100 configured to slice a 3D model and prepare the sliced model for manufacturing, according to one embodiment of the invention. As shown, the computing system 100 includes, without limitation, a computer system 102 and input/output (I/O) devices 116. The computer system 102 includes a memory 102, storage 106, a central processing unit (CPU) 110, an I/O device interface 112, a network interface 114 and a bus 108. The I/O device interface 112 interfaces with the I/O devices 116 (e.g., keyboard, display and mouse devices).

CPU 110 retrieves and executes programming instructions stored in the memory 102. Similarly, CPU 110 stores and retrieves application data residing in the memory 102. The bus 108 transmits programming instructions and application data between the CPU 110, I/O devices interface 112, storage 106, network interface 114 and memory 102. CPU 110 is included to be representative of a single CPU, multiple CPUs, a single CPU having multiple processing cores, and the like. And the memory 102 is generally included to be representative of a random access memory. The storage 106 may be a disk drive storage device. Although shown as a single unit, the storage 106 may be a combination of fixed and/or removable storage devices, such as magnetic disc drives, solid state drives (SSD), removable memory cards, optical storage, network attached storage (NAS), or storage volumes mounted over a storage area-network (SAN), etc.

As shown, the memory 102 includes a slicing engine 120. The slicing engine 120 slices 3D models and prepares the sliced models for manufacturing. To perform the slicing and preparation operations, the slicing engine 120 includes a slice generating module 122, a connector module 124, a labeling module 126, a layout module 128 and an assembly instructions module 130.

In operation, a user selects a pre-defined 3D model, such as the 3D model represented by the 3D geometry 118 stored in storage 106, for slicing. The user also identifies at least one plane that defines an axis along which the 3D model is to be sliced (referred to herein as the "slice axis"). Given the 3D model and at least one slice axis, the slice generating module 122 generates two or more slices of the 3D model, each slice having at least one polygonal part. A 3D model is sliced either along one slice axis, referred to herein as "one-way slicing," or along two slice axes, referred to herein as "two-way slicing." The techniques implemented by the slice generating module 122 for one-way slicing the 3D model is described in greater detail in conjunction with FIGS. 4A, 4B, 5 and 6. The techniques implemented by the slice generating module 122 for two-way slicing the 3D model is described in greater detail in conjunction with FIGS. 11-13.

Once the slices of a 3D model are generated, the connector module 124 analyzes the slices to determine how polygonal parts across different slices connect to one another to reform the 3D model. Each polygonal part in a slice connects with at least one polygonal part included in a preceding or subsequent slice. A pair of polygonal parts included in different slices that are to be connected are referred to herein as a "unique pair of consecutive polygonal parts." For each unique pair of consecutive polygonal parts, the connector module 124 identifies the locations on each polygonal part in the unique pair where the polygonal parts should be physically connected (referred to herein as the "connection locations associated with the pair"). The technique implemented by the connector module 124 for identifying the connection locations associated with a unique pair of consecutive polygonal parts is described in greater detail in conjunction with FIGS. 7A-7D and 8. The technique implemented by the connector module 124 for identifying the connection locations on slices of a two-way sliced 3D model is described in greater detail in conjunction with FIGS. 14A and 14B.

Given the slices of the 3D model and the connection locations associated with each unique pair of consecutive polygonal parts, the labeling module 126 generates a set of labels for each polygonal part included in the slices of the 3D model. A set of labels for a particular polygonal part includes a part label that identifies the part, a slice label that identifies the slice of the 3D model to which the part belongs and one or more connector labels identifying the connection locations associated with the pair of polygonal parts to which the part belongs. In one embodiment, the connection locations associated with a unique pair of consecutive polygonal parts are identified by the same connector labels.

The layout module 128 analyzes each polygonal part included in the slices of the 3D model to determine a layout of the polygonal parts on one or more sheets of a manufacturing material selected by the user (referred to herein as the "manufacturing material"). The layout module 128 determines a layout that makes efficient use of the material. The technique implemented by the layout module 128 for laying out the polygonal parts on the manufacturing material are described in greater detail below in conjunction with FIGS. 9 and 10.

Once the layout is determined, the outlines of the polygonal parts included in the slices of the 3D model are printed on to sheets of the manufacturing material according to the layout determined by the layout module 128. The user is then able to cut out the polygonal parts and connect the parts according to the connection locations to create a physical representation of the 3D model. The assembly instructions module 130 generates documentation that assists the user in connecting the polygonal parts to create the physical representation. The documentation generated by the assembly instructions module 130 may be in the form of a video, audio, text, images or a combination thereof.

Figure 2:
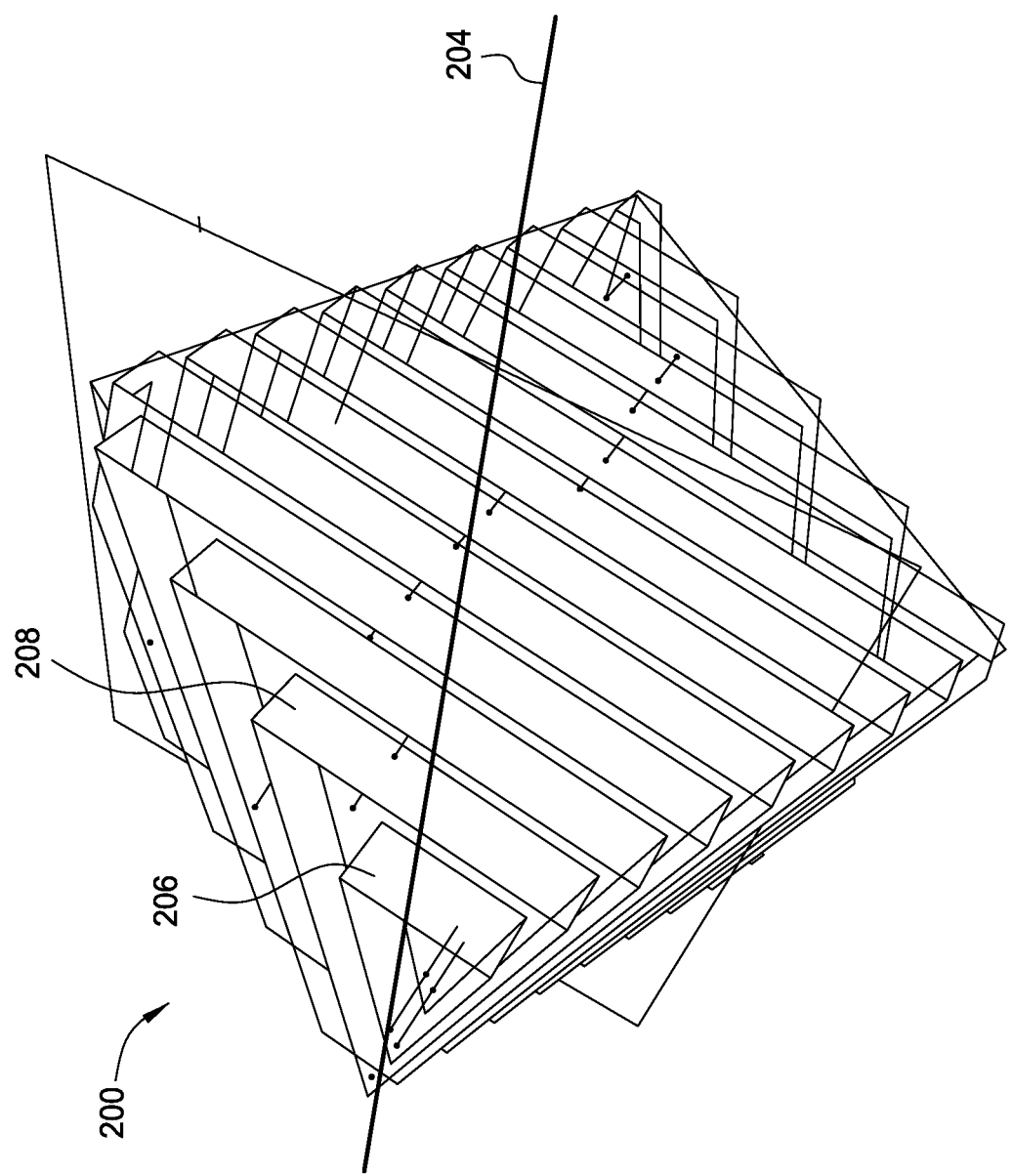
FIG. 2 illustrates a 3D model of a cube that is sliced by the slicing engine, according to one embodiment of the invention.

FIG. 2 illustrates a 3D model of a cube 200 that is sliced by the slicing engine 120, according to one embodiment of the invention. As shown, the 3D model of the cube 200 is sliced along the slice axis 204, where slice 206 and slice 208 are consecutively placed slices in the sliced model. Further, both slice 206 and slice 208 have only one polygonal part each. Once manufactured, the two polygonal parts of slice 206 and slice 208 are to be connected at pre-identified connection points to form a portion of the 3D model of the cube 200.

Figure 3:
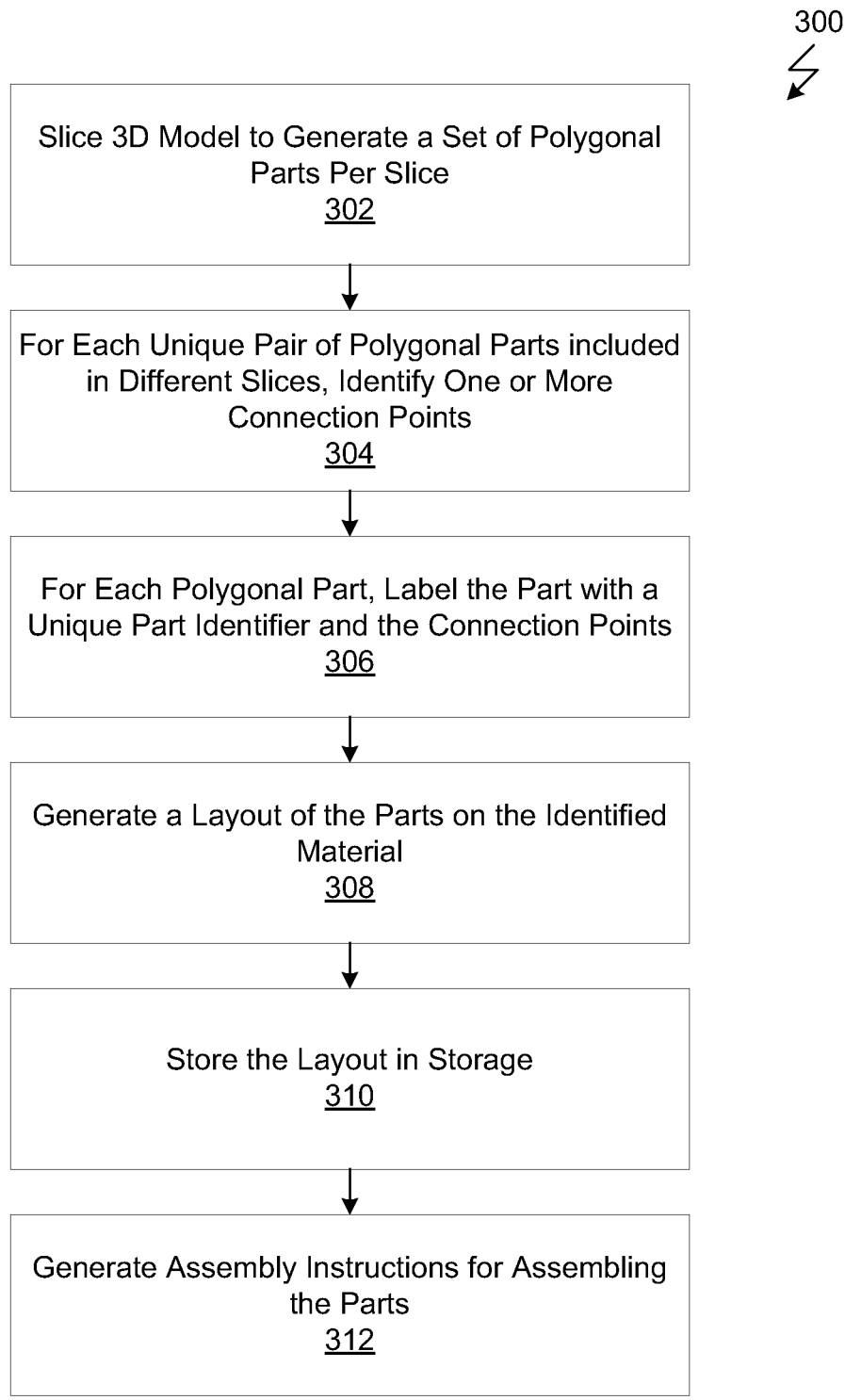
FIG. 3 illustrates a method for slicing a 3D model and preparing the sliced model for manufacturing, according to one embodiment of the invention.

FIG. 3 illustrates a method for slicing a 3D model and preparing the sliced model for manufacturing, according to one embodiment of the invention. Although the method steps are described in conjunction with the system for FIG. 1, persons skilled in the art will understand that any system configured to perform the method steps, in any order, is within the scope of the invention.

The method 300 begins at step 302, where the slice generating module 122 generates two or more slices of the 3D model, each slice having a set of polygonal parts. At step 304, the connector module 124, for each unique pair of consecutive polygonal parts, identifies the connection locations associated with the unique pair indicating the location where the polygonal parts are to be physically attached At step 306, given the slices of the 3D model and the connection locations associated with each unique pair of consecutive polygonal parts, the labeling module 126 generates a set of labels for each polygonal part included in the slices of the 3D model. The set of labels for a particular polygonal part includes a part label that identifies the part, a slice label that identifies the slice of the 3D model to which the part belongs and one or more connector labels identifying the connection locations associated with the pair of polygonal parts to which the part belongs.

At step 308, the layout module 128 analyzes each polygonal part included in the slices of the 3D model to determine a layout of the polygonal parts on one or more sheets of a manufacturing material selected by the user. At step 310, the layout determined by the layout module 128 is stored in storage 106. At step 312, the assembly instructions module 130 generates documentation that assists the user in connecting the polygonal parts to create the physical representation. The layout may be retrieved by a user for printing on the manufacturing material. The user is then able to cut out the polygonal parts and, based on the assembly instructions, connect the parts according to the connection locations to create a physical representation of the 3D model.

One-Way Slicing of a 3D Model

Figure 5A:
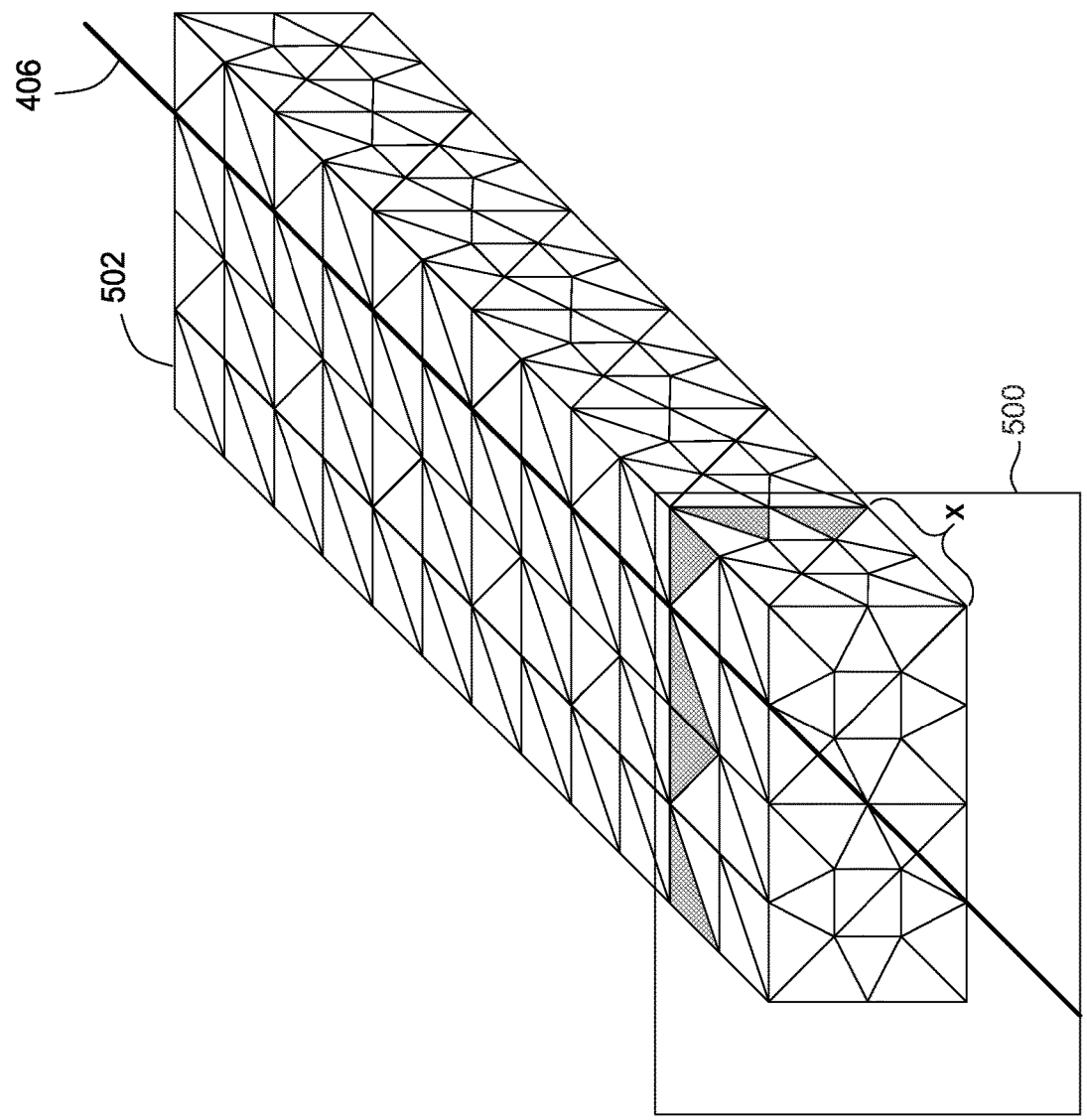
FIG. 5A illustrates the 3D model of FIG. 4 as a triangulated mesh, according to one embodiment of the invention.

FIG. 4 illustrates a slice plane 404 selected by a user for one-way slicing the 3D model of a cuboid 402, according to one embodiment of the invention. The user, by operating a user interface (not shown), is able to draw a slice plane for slicing the 3D model of the cuboid 402 (referred to herein as the "3D model 402"). Further, once the slice plane 404 is drawn, the user is able modify (rotate, move, etc.) the slice plane 404 to her satisfaction. Once the user has finalized the slice plane 404, the slice generating module 122 determines the slice axis 406 as the axis orthogonal to the slice plane 404. FIGS. 5A-6 describe in detail how the slice generating module 122 slices the 3D model 402 based on the slice axis 406.

FIG. 5A illustrates the 3D model 402 of FIG. 4 as a triangulated mesh 502, according to one embodiment of the invention. To generate a single slice of the 3D model 402, the slice generating module 122 draws a plane 500 at a pre-determined width interval on the triangulated mesh 502, where the plane 500 is orthogonal to the slice axis 406. Next, the slice generating module 122 identifies a set of triangles in the triangulated mesh 502 that each has a line segment that intersects the drawn plane. For example, at width interval x, the slice generating module 122 draws a plane 500 that is orthogonal to the slice axis 406. The slice generating module 122 then identifies the set of triangles in the triangulated mesh, where each triangle in the set of triangles has a line segment that intersects the plane 500. For illustrative purposes, the set of triangles identified by the slice generating module 122 are shaded in FIG. 5A. Once the set of triangles that intersect the plane is identified, the slice generating module 122 stitches together the line segments of the set of triangles that intersect the plane to form the boundary of the slice. The slice generating module 122 performs the above operations at regular width intervals on the triangulated mesh 502 to generate a set of slices of the 3D model 402.

Figure 5B:
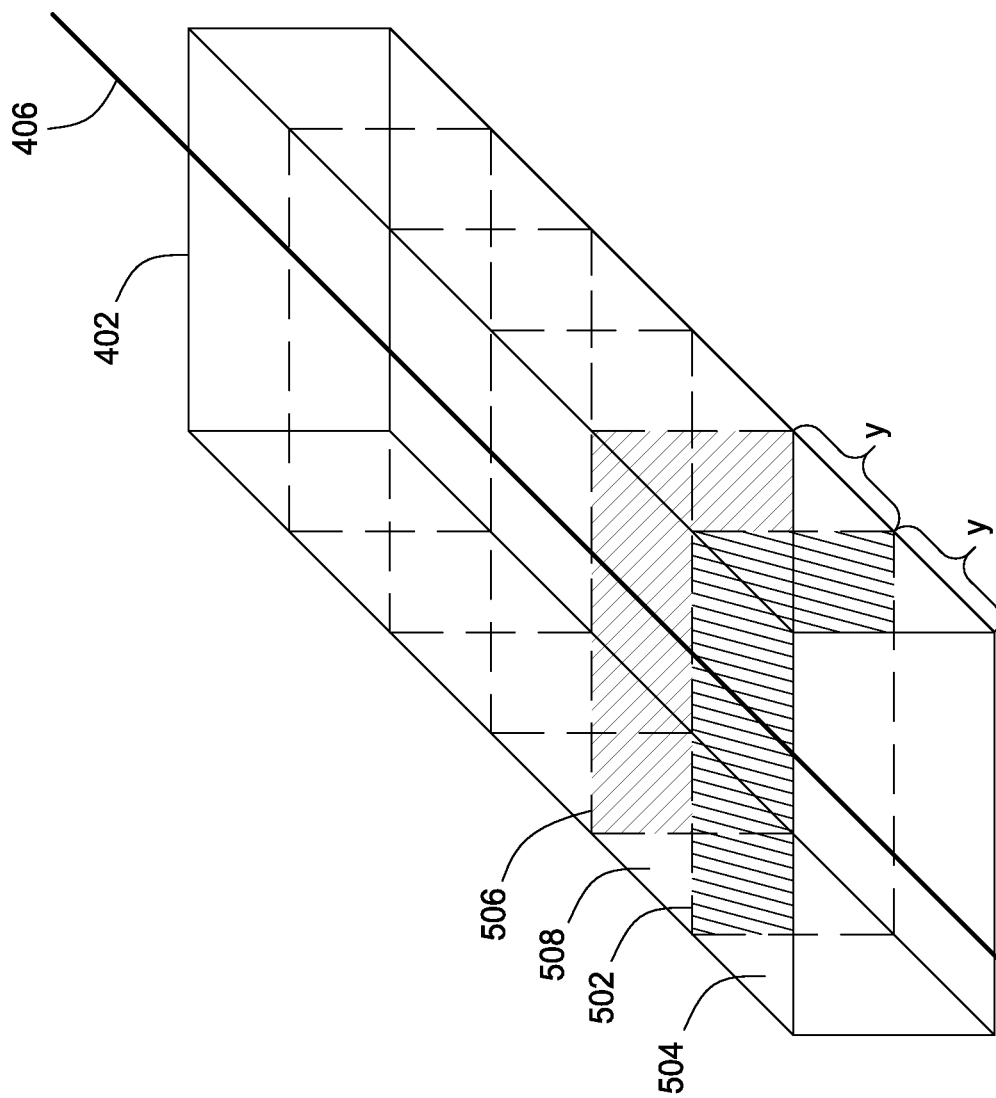
FIG. 5B illustrates the 3D model of FIG. 4 sliced by the slice generating module 122, according to one embodiment of the invention.
Figure 6:
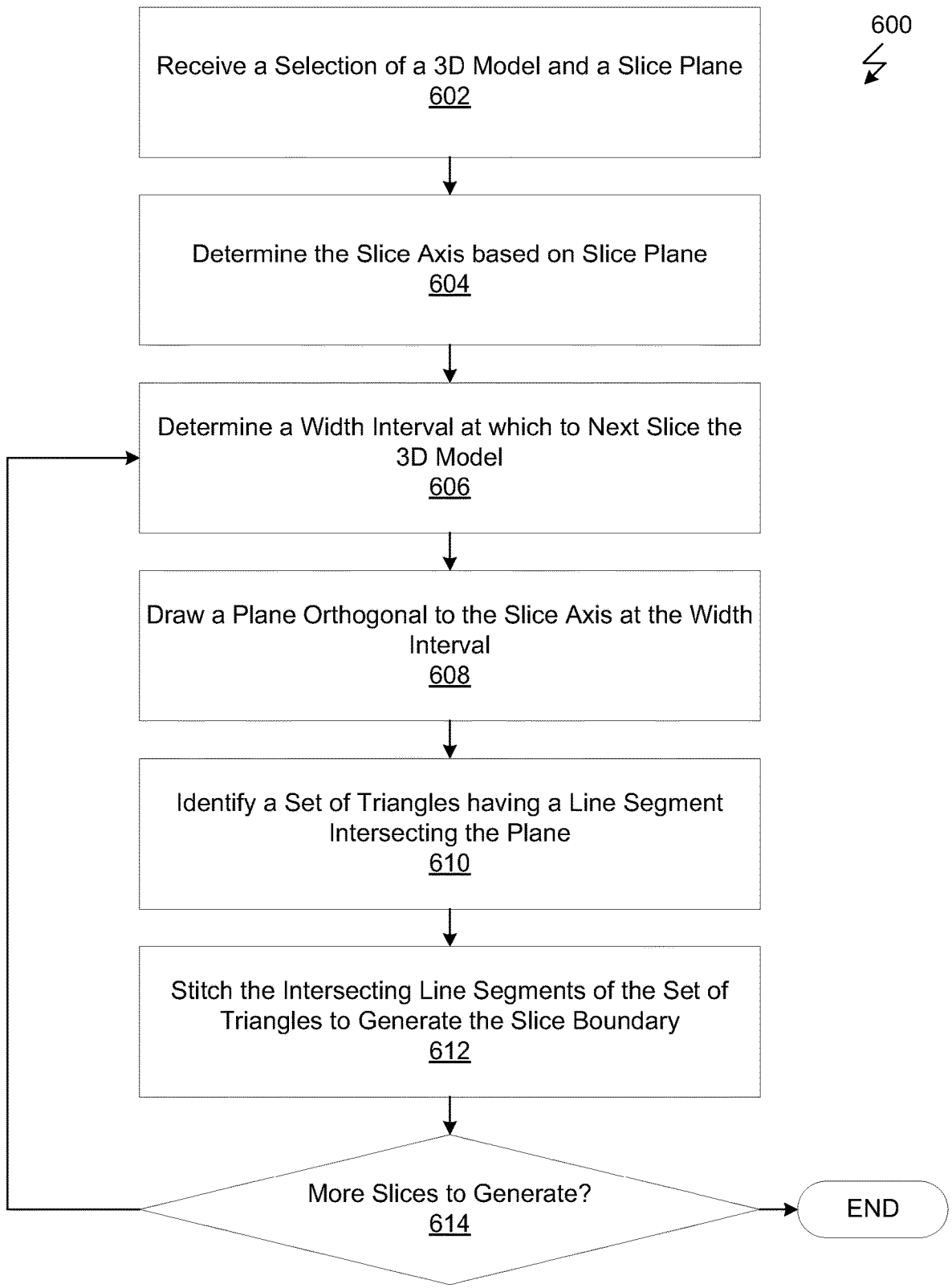
FIG. 6 illustrates a method for slicing a 3D model using a one-way slicing technique, according to one embodiment of the invention.

FIG. 5B illustrates the 3D model 402 of FIG. 4 sliced by the slice generating module 122, according to one embodiment of the invention. As shown, the 3D model 402 is sliced along the slice axis 406 at regular width intervals y. Slice boundary 502 identified by the slice generating module 122 using the technique described in conjunction with FIG. 5A is associated with slice 504 of the sliced 3D model 402. Similarly, slice boundary 506 identified by the slice generating module 122 using the technique described in conjunction with FIG. 5A is associated with slice 508 of the sliced 3D model 402.

The width interval at which the slice generating module 122 slices the 3D model 402 is either the same across all slices or varies across different slices. In one embodiment, the width intervals at which the slice generating module 122 slices the 3D model 402 is determined based on a thickness of a material using which the 3D model is to be manufactured. In an alternate embodiment, the user specifies an offset indicating the thickness of the slices and therefore the width interval. In yet another embodiment, the slice generating module 122 determines the thickness of each slice based on the dimensions of the 3D model 402.

FIG. 6 illustrates a method for slicing a 3D model using a one-way slicing technique, according to one embodiment of the invention. Although the method steps are described in conjunction with the system for FIG. 1, persons skilled in the art will understand that any system configured to perform the method steps, in any order, is within the scope of the invention.

The method 600 begins at step 602, where the slice generating module 122 receives a selection of a 3D model and a slice plane from a user. At step 604, determines the slice axis as the axis orthogonal to the slice plane received at step 602. At step 606, the slice generating module 122 determines a width interval at which a next slice of the 3D model is to be generated. In one embodiment, the width interval is based on an offset parameter specified by the user. In alternate embodiment, the slice generating module 122 determines the width interval based on the dimensions of the 3D model, a manufacturing material to be used for manufacturing or any other technically feasible means.

Once the width interval at which the next slice of the 3D model is to be generated is determined, the slice generating module 122, at step 608, draws a plane on the 3D model that is orthogonal to the slice axis determined at step 604. At step 610, the slice generating module 122 identifies a set of triangles in the triangulated mesh representation of the 3D model, where each triangle in the set of triangles has a line segment that intersects the plane drawn at step 608. Next, at step 612, the slice generating module 122 stitches together the line segments of the set of triangles that intersect the plane to form the boundary of the slice. The slice of the 3D model is then stored.

At step 614, the slice generating module 122 determines whether more slices of the 3D model are to be generated. If so, then the method 600 returns to step 606 and the method 600 loops through steps 606-614 until no more slices of the 3D model are to be generated. When no more slices are to be generated, the method 600 ends.

FIGS. 7A-7D illustrate a technique for identifying connection points for connecting two polygonal parts included in two different slices of the 3D model, according to one embodiment of the invention.

In operation, the connector module 124 analyzes the slices of the 3D model to determine how polygonal parts across different slices connect to one another to reform the 3D model. Again, a pair of polygonal parts included in different slices that are to be connected are referred to herein as a "unique pair of consecutive polygonal parts." For purposes of discussion, polygonal part 703 and polygonal part 705 are a unique pair of consecutive polygonal parts. In one embodiment, polygonal part 703 is included in slice 504 of FIG. 5B and polygonal part 705 is included in slice 508.

Figure 7B:
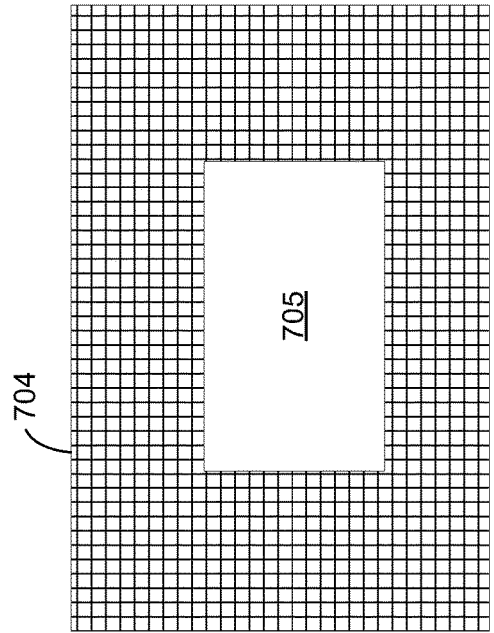
FIGS. 7A-7D illustrate a technique for identifying connection points for connecting two polygonal parts included in two different slices of the 3D model, according to one embodiment of the invention.
Figure 7D:
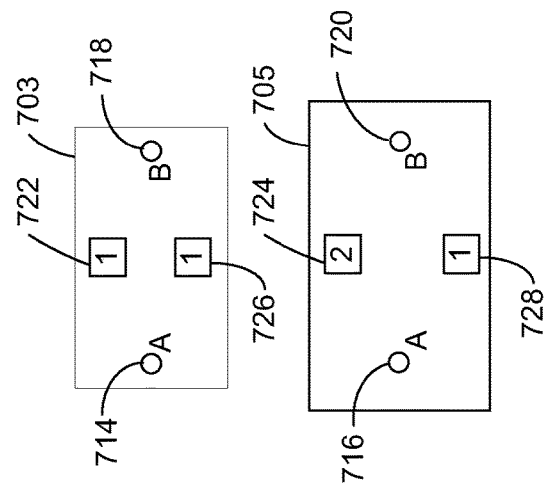
Figure 7A:
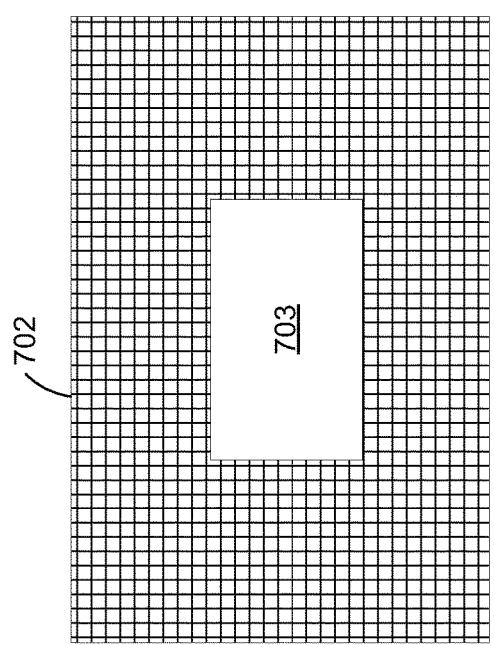

To identify connection points associated with polygonal part 703 and polygonal part 705, the connector module 124 first places the polygonal part 703 on a grid 702 and traces the outline of the polygonal part 703 onto the grid 702, as shown in FIG. 7A. Similarly, the connector module 124 places the polygonal part 705 on a grid 704 and traces the outline of the polygonal part 705 onto the grid 704, as shown in FIG. 7B.

Figure 7C:
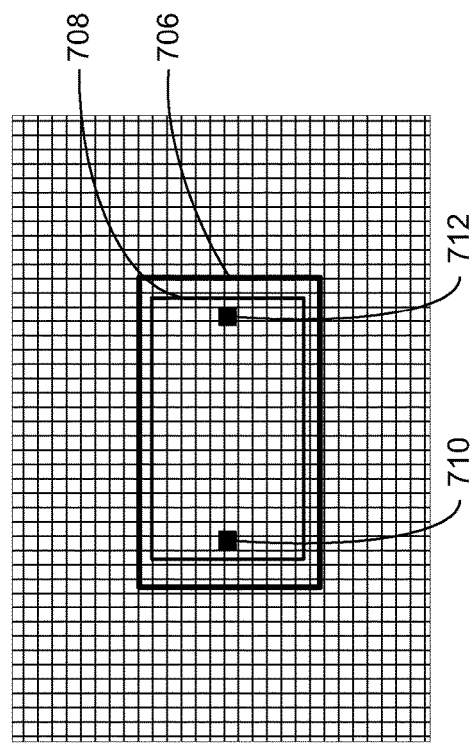

The connector module 124 then overlays the outline 706 of the polygonal part 705 onto the outline 708 of the polygonal part 703, as shown in FIG. 7C. Once the outlines are overlaid, the connector module 124 locates a grid location 712 close to one edge of the smaller outline, i.e., outline 708. The connector module 124 then locates a grid location 710 close to the opposite edge of the smaller outline, i.e., outline 708. The connector module 124 then identifies the locations on the polygonal parts 703 and 705 corresponding to the grid locations 710 and 712. The identified locations are the locations of the connection points associated with polygonal parts 703 and 705 indicating the location where polygonal parts 703 and 705 are to be attached.

As noted, the connector module 124 finds connection points between one-way slices. To do so, in one embodiment, the connector module 124 connects adjacent slice pairs with a pair of holes. Further, the orientation for a pair of holes is North/South on even and East/West on odd pairs (that is the algorithm performed by the connector module 124 may alternate to avoid collisions and better identify part mates). Further, the connector modules may also record previous holes on the grid. Doing so prevents collisions in the holes for the next pair.

In one embodiment, for a particular pair of consecutive polygonal parts, the grid locations corresponding to connection points for that pair are located along the x-axis of the grid. In such an embodiment, for a directly subsequent pair of consecutive polygonal parts, the grid locations corresponding to connection points for that pair are located along the y-axis of the grid.

The connector module 124 performs the connection point analysis described above for each unique pair of polygonal parts. Once the connection points for all the unique pair of polygonal parts included in the slices of the 3D model are determined, the labeling module 126 generates a set of labels for each polygonal part included in the slices of the 3D model. The set of labels for a particular polygonal part includes a part label that identifies the part, a slice label that identifies the slice of the 3D model to which the part belongs and one or more connector labels identifying the connection locations associated with the pair of polygonal parts to which the part belongs.

As shown in FIG. 7D, the labeling module 126 labels the connection points 714, 716, 718 and 720 associated with polygonal parts 703 and 705. The labels for corresponding connection points are the same, such that connection point 714 and connection point 716 correspond to one another and are therefore labeled the same, i.e., "A." Similarly, connection point 718 and connection point 720 correspond to one another and are therefore labeled the same, i.e., "B." As also shown in FIG. 7D, the labeling module 126 labels the individual polygonal parts 703 and 705 with a slice number and a part number. Polygonal part 703 is labeled with a slice number 722 that indicates the particular slice to which the polygonal part 703 belongs, i.e., slice number "1." The polygonal part 703 is also labeled with a part number 726 indicating the particular part number associated with the part within slice number "1." Similarly, polygonal part 705 is labeled with a slice number 724 that indicates the particular slice to which the polygonal part 703 belongs, i.e., slice number "2." The polygonal part 703 is also labeled with a part number 728 indicating the particular part number associated with the part within slice number "2."

Persons skilled in the art would readily recognize that any labeling technique may be implemented by the labeling module 126 including shading and alphabetical ordering.

Figure 8:
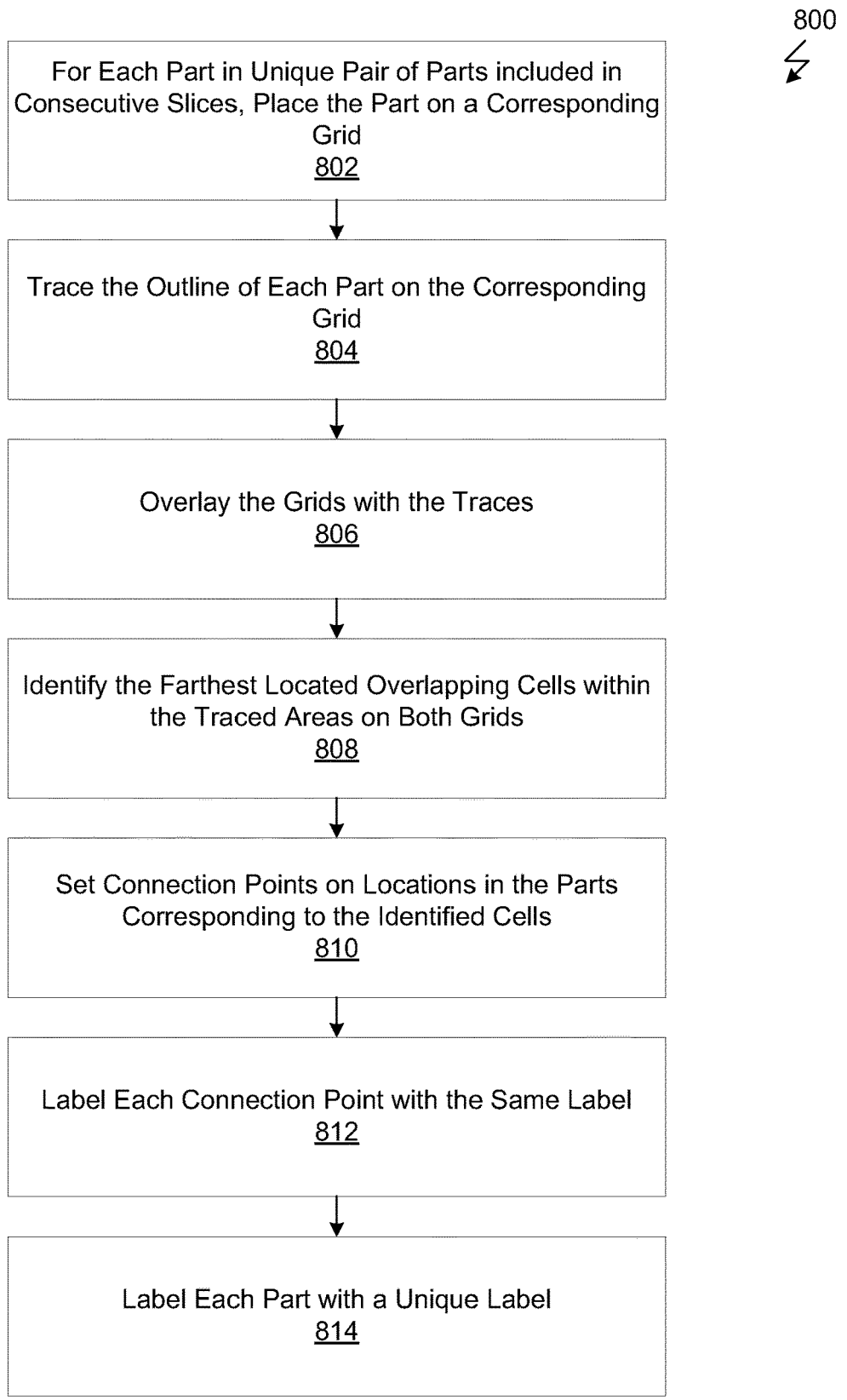
FIG. 8 illustrates a method for identifying connections points associated with a part of consecutive polygonal parts, according to one embodiment of the invention.

FIG. 8 illustrates a method for identifying connections points associated with a pair of consecutive polygonal parts, according to one embodiment of the invention. Although the method steps are described in conjunction with the system for FIG. 1, persons skilled in the art will understand that any system configured to perform the method steps, in any order, is within the scope of the invention.

The method 800 begins at step 802, where the connector module 124, for each polygonal part of a unique pair of consecutive polygonal parts, places the polygonal part on a grid (referred to herein as "the corresponding grid"). At step 804, the connector module 124 traces the outline of each polygonal part on the corresponding grid.

At step 806, the connector module 124 overlays the outline of a first polygonal part onto the outline of a second polygonal part. At step 808, the connector module 124 locates the farthest grid locations close to each edge of the smaller outline. At step 810, the connector module 124 identifies the locations on the polygonal parts corresponding to the grid locations located at step 808. The identified locations are the locations of the connection points associated with polygonal parts indicating the location where polygonal parts are to be attached.

At step 812, the labeling module 126 generates the same label for each connection point on the polygonal parts identified at step 810. In addition, at step 814, the labeling module 126 generates a unique label for each polygonal part that uniquely identifies the part.

Figure 9:
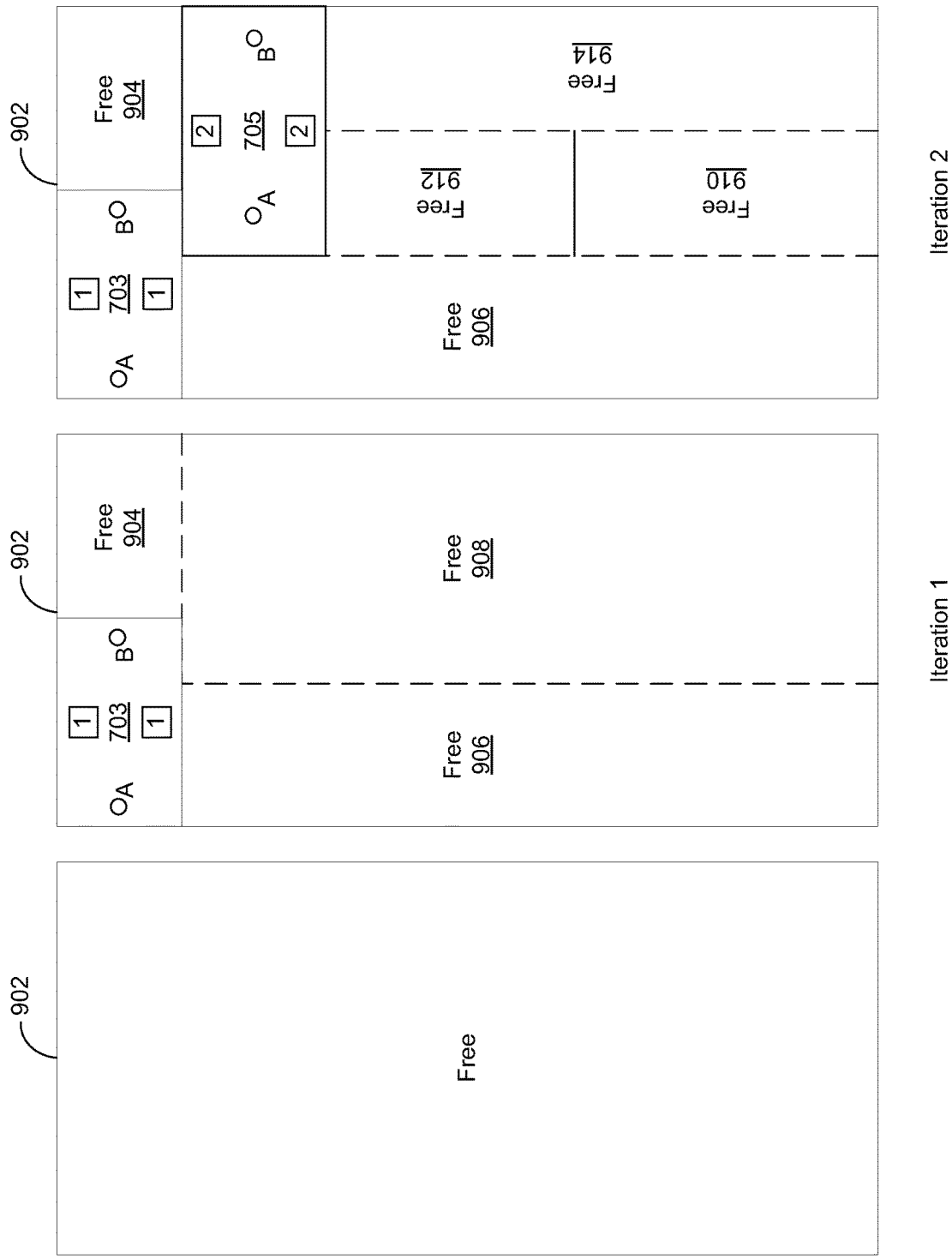
FIG. 9 illustrates a technique for laying out polygonal parts included in different slices of the 3D model on manufacturing material, according to one embodiment of the invention.

FIG. 9 illustrates a technique for laying out polygonal parts included in different slices of the 3D model on manufacturing material selected by the user, according to one embodiment of the invention. The technique is described below for laying out polygonal parts 703 and 705 on a virtual representation of a sheet of stock material 902.

In operation, the layout module 128 tracks the free space available in each sheet of manufacturing material already being occupied, at least in-part, by other polygonal parts. The free space in a particular sheet is tracked as a set of free portions. In one embodiment, the layout module 128 tracks the free space in a tree data structure. When laying out a particular polygonal part, such as polygonal part 703, the layout module 128 first determines the measurements of the polygonal part. Based on the measurement, the layout module 128 then selects a sheet of manufacturing material already being occupied, at least in-part, by other polygonal parts that has enough space for the polygonal part. If no such sheet exists, then the layout module 128 selects a new sheet on which the polygonal part is to be laid out.

Stated again, the layout module 128 arranges space into a tree and records the largest free space in each child of the tree at every level. Doing so make is it easy to determine which child has enough space to satisfy a request. An unsuccessful request adds another stock page. Further, parts that are bigger than stock pages are automatically split into page size pieces with joinery. In the case where the part is larger in both dimensions, then it is split into a grid of subparts along with the necessary joinery. In one embodiment, the layout module 128 finds the smallest free rectangle (i.e., node in the tree) large enough to accommodate the For discussion purposes, the layout module 128 selects sheet 902, which is unoccupied, for laying out polygonal part 703. Next, the layout module 128 places the polygonal part 703 on a free portion of the selected sheet 902. Because the sheet 902 is not completely occupied by the polygonal part 703, the layout module 128 divides the remaining free space in the sheet 902 into three different free portions 904, 906 and 908. The free space in the sheet 902 is then updated to reflect the portion occupied by the polygonal part and the new free portions 904, 906 and 908 generated as a result.

For laying out polygonal part 705, the layout module 128 identifies based on the dimensions of polygonal part 705 a free portion of the free portion 904, 906 and 908 in sheet 902 into which the polygonal part 705 can be placed. Given the dimensions of the polygonal part 705, the layout module 128 determines that the polygonal part 705 can only be placed into free portion 908. The layout module 128 then places the polygonal part 705 into free portion 908 and divides the remaining free space in free portion 908 into three new free portions 910, 912 and 914. The free space in the sheet 902 is then updated to reflect the portion occupied by the polygonal part and the new free portions 910, 912 and 914 generated as a result.

The layout module 128 performs multiple iteration of the technique described above, and, at each iteration, a different polygonal part of the 3D model is laid on a sheet of manufacturing material. The layout of the polygonal parts on sheets of the manufacturing material is then stored in storage 106.

Figure 10:
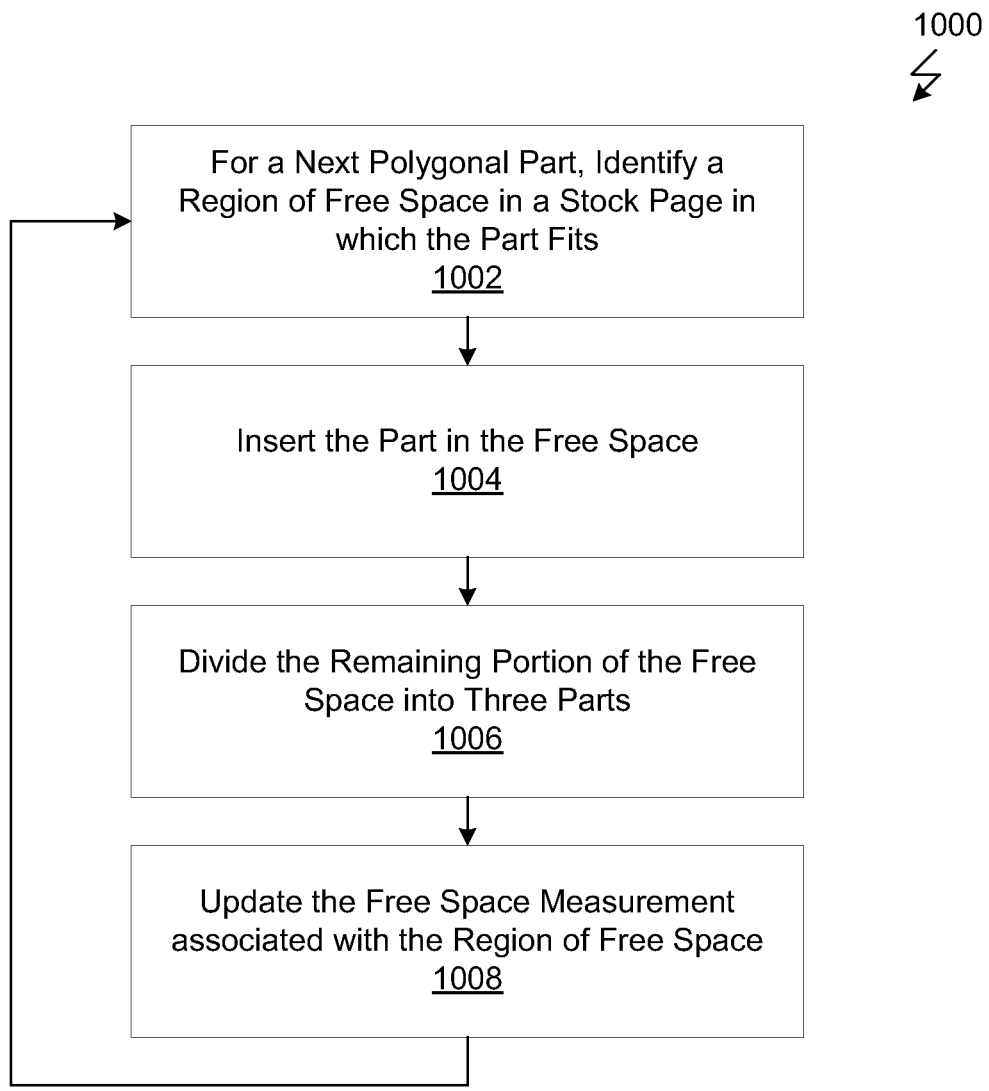
FIG. 10 illustrates a method for laying out polygonal parts on manufacturing material, according to one embodiment of the invention.

FIG. 10 illustrates a method for laying out polygonal parts on manufacturing material, according to one embodiment of the invention. Although the method steps are described in conjunction with the system for FIG. 1, persons skilled in the art will understand that any system configured to perform the method steps, in any order, is within the scope of the invention.

The method 1000 begins at step 1002, where the layout module 128, for a next polygonal part in the sliced model, identifies based on the dimensions of the polygonal part a free portion in a stock page into which the polygonal part fits. At step 1004, the layout module 128 places the polygonal part into the free portion and divides the remaining free space in the free portion into three new free portions. At step 1008, the layout module 128 updates the free space associated with the stock page to reflect the portion occupied by the polygonal part and the new free portions generated as a result.

Two Way Slicing of a 3D Model

As discussed above, a 3D model may be sliced along two slice axes, referred to herein as "two-way slicing." The following discussion describes three different types of two-way slicing techniques, waffle slicing, spline slicing and radial slicing. The technique implemented to identify connection points on slices generated via a two-way slicing mechanism is also described.

Figure 11:
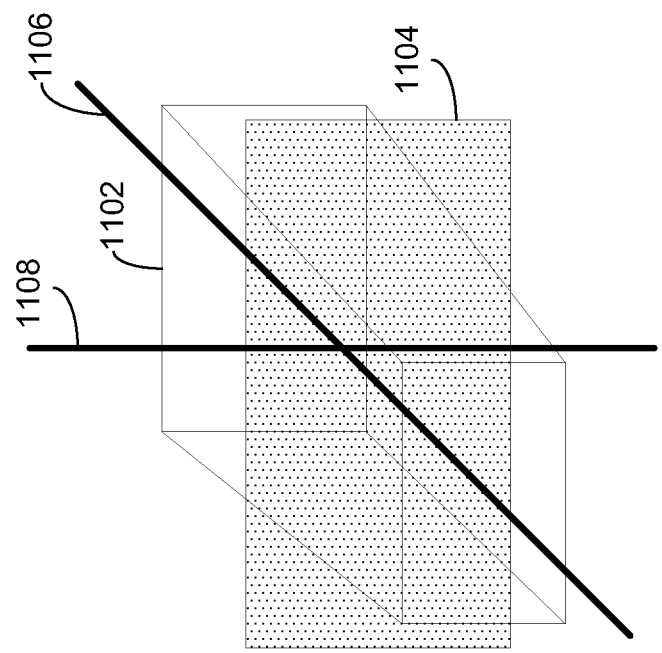
FIG. 11 illustrates a slice plane selected by a user for waffle slicing a 3D model, according to one embodiment of the invention.

FIG. 11 illustrates a slice plane 1104 selected by a user for waffle slicing a 3D model 1102, according to one embodiment of the invention. The user, by operating a user interface (not shown), is able to draw a slice plane for slicing the 3D model 1102. Further, once the slice plane 1104 is drawn, the user is able modify (rotate, move, etc.) the slice plane 1104 to her satisfaction. Once the user finalizes the slice plane 1104, the slice generating module 122 determines the primary slice axis 1106 as the axis orthogonal to the slice plane 1104. The slice generating module 122 also determines the orthogonal slice axis 1108 as the axis orthogonal to the primary slice axis 1104 (or parallel to the slice plane 1104).

In addition, the slice generating module 122 determines the value of the stock depth parameter, i.e., the depth of the particular stock material with which the 3D model is to be built. The slice generating module 112 also determines a value for a slice spacing parameter that indicates the spacing between each slice of the sliced 3D model 1102. In one embodiment, the value for the slice spacing parameter is provided by the user.

The slice generating module 122 slices the 3D model 1102 based on the primary slice axis 1106, the stock depth parameter and the slice spacing parameter. The technique implemented by the slice generating module 122 for slicing the 3D model 1102 is the same as the technique described above in conjunction with FIGS. 5A and 6. Note, the slots need some spacing between slices, i.e., slice spacing must be greater than the sock depth, allowing for room slots in-between the slices. Next, the slice generating module 122 slices the 3D model 1102 based on the secondary slice axis, i.e., the slice axis orthogonal to the primary slice axis 1106. Again, each generated slice has a depth that is equivalent to the stock depth parameter, and the spacing between consecutive slices is equivalent to the slice spacing parameter.

Figure 12:
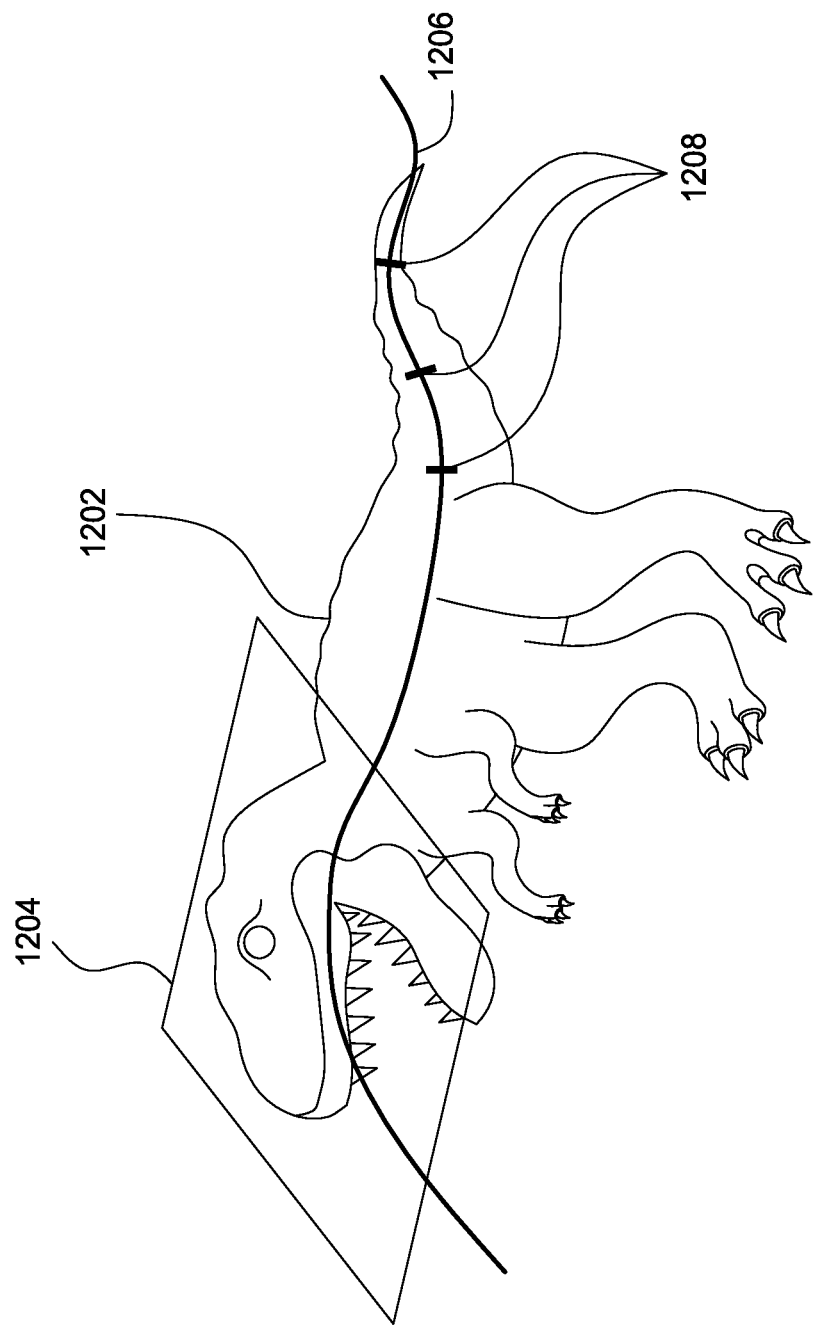
FIG. 12 illustrates a slice plane selected by a user for splice slicing a 3D model, according to one embodiment of the invention.

FIG. 12 illustrates a slice plane 1204 selected by a user for splice slicing a 3D model 1202, according to one embodiment of the invention. The user, by operating a user interface (not shown), is able to draw the slice plane 1204 for slicing the 3D model 1202. Further, once the slice plane 1204 is drawn, the user is able modify (rotate, move, etc.) the slice plane 1204 to her satisfaction. Once the user has finalized the slice plane 1204, the slice generating module 122 determines the primary slice axis as the axis orthogonal to the slice plane 1204. The user, in addition to the slice plane 1204, also draws a spline 1206 through the 3D model 1202. In one embodiment, the user draws the spline 1206 by identifying various points along the 3D model 1202 that are then connected by the slice generating module 122 to form the spline 1206.

In addition, the slice generating module 122 determines the value of the stock depth parameter, i.e., the depth of the particular stock material with which the 3D model is to be built. The slice generating module 122 also determines a value for a slice spacing parameter that indicates the space between each slice of the sliced 3D model 1102. In one embodiment, the value for the slice spacing parameter is provided by the user. In alternate embodiments, the value for the slice spacing parameter is based on the value of the stock depth parameter.

The slice generating module 122 slices the 3D model 1204 based on the primary slice axis, the stock depth parameter and the slice spacing parameter. The technique implemented by the slice generating module 122 for slicing the 3D model 1204 along the primary slice axis is the same as the technique described above in conjunction with FIGS. 5A and 6. Each slice has a depth that is equivalent to the stock depth parameter, and the spacing between consecutive slices is equivalent to the slice spacing parameter.

Next, the slice generating module 122 slices the 3D model 1202 based on the secondary slice axis, i.e., spline 1206. To slice the 3D model 1202 based on the spline 1206, the slice generating module 122, at each interval of the slice spacing parameter, determines the axis orthogonal to the spline 1206 drawn by the user. The slice generating module 122 then slices the 3D model 1202 at that interval of the slice spacing parameter according to the determined axis. Again, each generated slice has a depth that is equivalent to the stock depth parameter, and the spacing between consecutive slices is equivalent to the slice spacing parameter.

Figure 13:
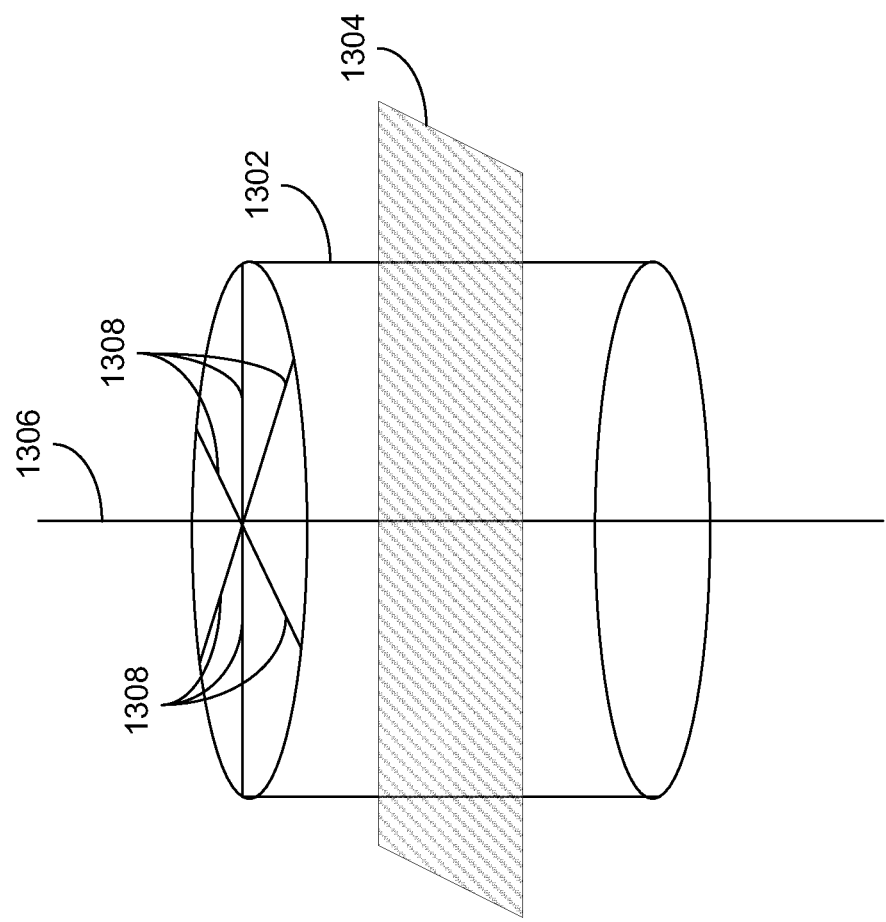
FIG. 13 illustrates a slice plane selected by a user for radially slicing a 3D model, according to one embodiment of the invention.

FIG. 13 illustrates a slice plane 1304 selected by a user for radially slicing a 3D model 1302, according to one embodiment of the invention. The user, by operating a user interface (not shown), is able to draw the slice plane 1304 for slicing the 3D model 1302. Further, once the slice plane 1304 is drawn, the user is able modify (rotate, move, etc.) the slice plane 1304 to her satisfaction. Once the user has finalized the slice plane 1304, the slice generating module 122 determines the primary slice axis 1306 as the axis orthogonal to the slice plane 1304.

In addition, the slice generating module 122 determines the value of the stock depth parameter, i.e., the depth of the particular stock material with which the 3D model is to be built. The slice generating module 112 also determines a value for a slice spacing parameter that indicates the space between each slice of the sliced 3D model 1302. Finally, the slice generating module 112 determines the number of radial slices to be created. In one embodiment, the values for the slice spacing parameter and the number of radial slices are provided by the user. In alternate embodiments, the values are based on the value of the stock depth parameter.

The slice generating module 122 slices the 3D model 1302 based on the primary slice axis 1304, the stock depth parameter and the slice spacing parameter. The technique implemented by the slice generating module 122 for slicing the 3D model 1302 along the primary slice axis is the same as the technique described above in conjunction with FIGS. 5A and 6. Each slice has a depth that is equivalent to the stock depth parameter, and the spacing between consecutive slices is equivalent to the slice spacing parameter.

Next, the slice generating module 122 radially slices the 3D model 1302 based on a set of secondary slice axes. In operation, the slice generating module 122 identifies a set of secondary slice axes 1308 that are orthogonal to the primary slice axis 1306 and equal to the number of radial slices determined by the slice generating module 122. The slice generating module 122 then slices the 3D model 1302 along each of the set of radial slice axes 1308 to generate radial slices. In the case of 3D model 1302, the slice generating module 122 generates six radial slices, one radial slice along each of the radial slice axis 1308.

Each slice generated via the waffle, spline or radial slicing techniques based on the primary slice axis is associated with a set of slices generated based on the secondary slice axis or axes ("referred to herein as "the set of complementary slices"). For example, in FIG. 13, slices generated based on primary slice axis 1306 are each associated with a set of complementary slices generated based on the set of secondary slice axes 1308. A complementary slice of a particular slice generated based on a primary slice axis is a slice that intersects with the particular slice.

Figure 14B:
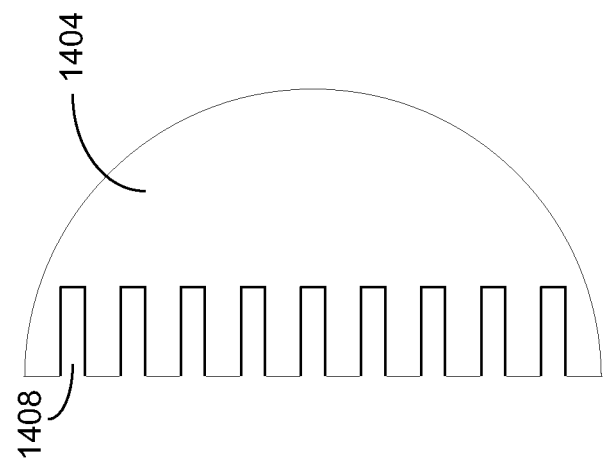
FIGS. 14A and 14B illustrate connection points on two slices of the two-way sliced 3D model, according to one embodiment of the invention.
Figure 14A:
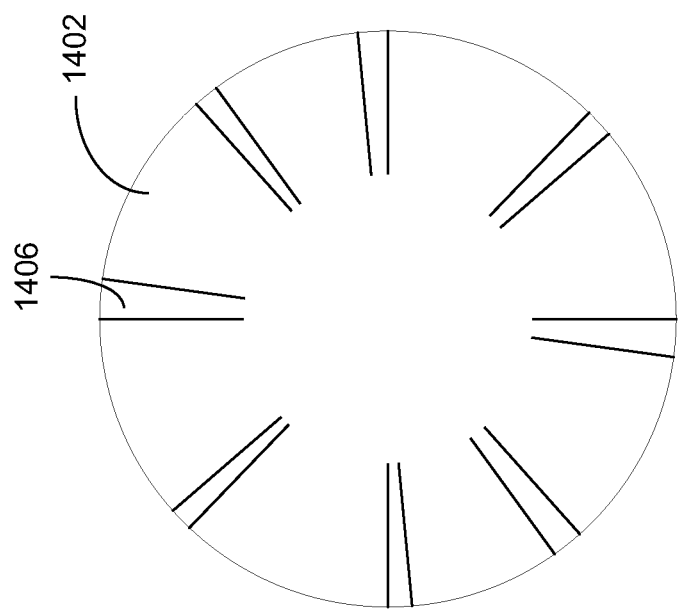

FIGS. 14A and 14B illustrate connection points on two slices of the two-way sliced 3D model 1302, according to one embodiment of the invention. As shown, primary slice 1402 is a slice of the 3D model 1302 along the primary slice axis 1304 and secondary slice 1404 is a slice of the 3D model 1302 along a radial slice axis from the set of secondary slice axes 1308. Secondary slice 1404 is a complementary slice to primary slice 1402.

To identify connection points for slices of a 3D model generated via two-way slicing, the connection module 124 first determines, for each slice generated based on a primary slice axis (referred to herein as the "the primary slice"), the associated set of complementary slices. For each complementary slice, the connection module 124 determines the location on the complementary slice and the primary slice where the complementary slice intersects with the primary slice. The connection module 124 then marks the identified location on both the complementary slice and the primary slice as the location where slots are to be cut after the slices are manufactured. To connect the manufactured slices, the user slides the slot on the complementary slice into the slot on the primary slice. For example, slot 1406 is located on primary slice 1402 where secondary slice 1404 intersects primary slice 1402. Thus, to connect primary slice 1402 and secondary slice 1404, the user slides slot 1406 into slot 1408.

Figure 15:
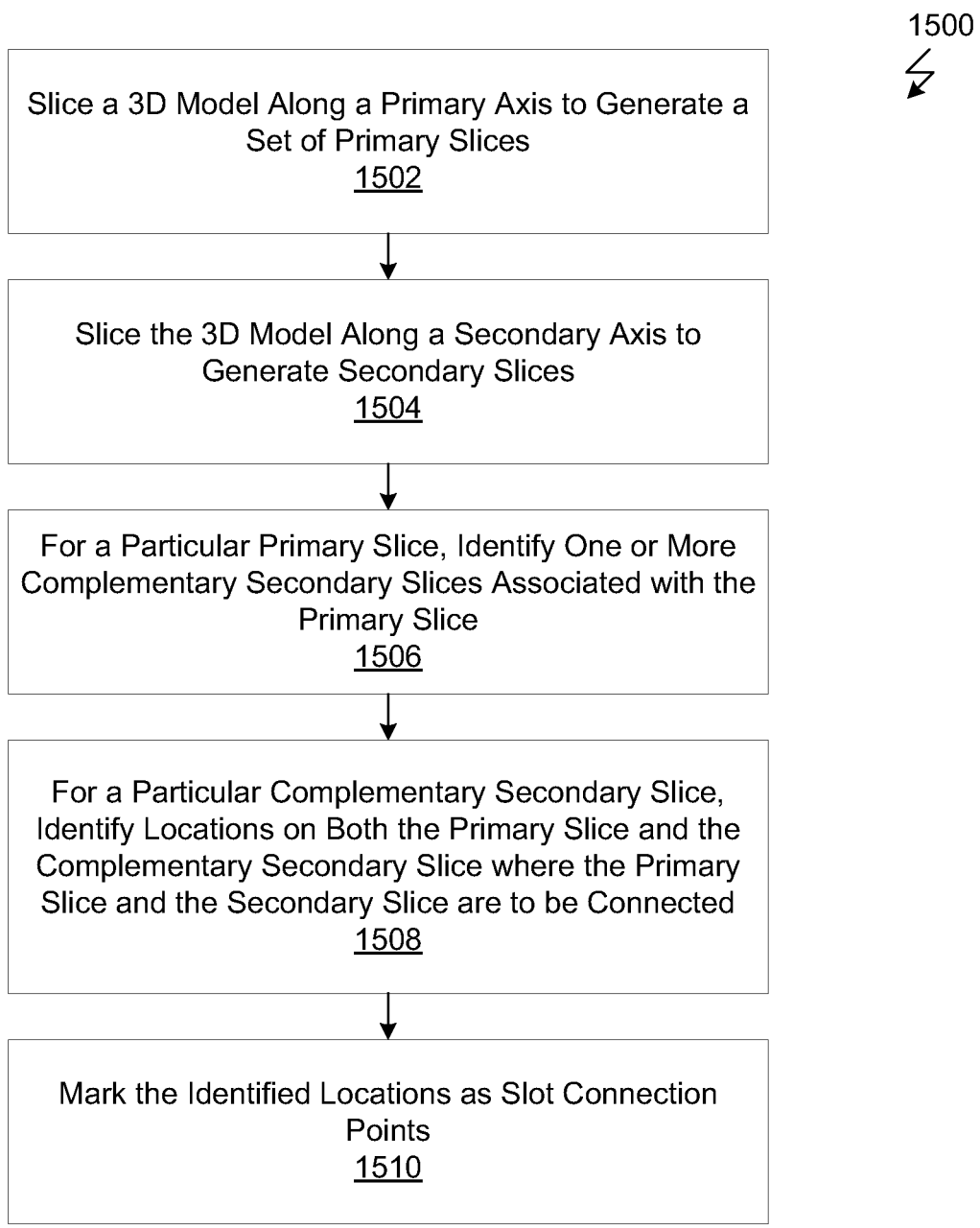
FIG. 15 illustrates a method for identifying connections points associated with two slices of a two-way sliced 3D model, according to one embodiment of the invention.

FIG. 15 illustrates a method for identifying connections points associated with two slices of a two-way sliced 3D model, according to one embodiment of the invention. Although the method steps are described in conjunction with the system for FIG. 1, persons skilled in the art will understand that any system configured to perform the method steps, in any order, is within the scope of the invention.

The method 1500 begins at step 1502, where the slice generating module 122 slices the 3D model along a primary axis defined by a user to generate a set of primary slices. At step 1504, the slice generating module 122 slices the 3D model along at least secondary axis defined by a user to generate a set of secondary slices. The techniques implemented by the slice generating module 122 to generate the set of primary slices and the set of secondary slices is described above in conjunction with FIGS. 11-13.

At step 1506, the connection module 124 identifies one or more complementary secondary slices associated with a particular primary slice. At step 1508, for a particular complementary secondary slice, the connector module 124, the connection module 124 determines the locations on the secondary slice and the primary slice where the slices intersect and are to be connected.

At step 1510, the connection module 124 marks the identified locations on both the secondary slice and the primary slice as slot connection points, i.e., the locations where slots are to be cut after the slices are manufactured. To connect the manufactured slices, the user slides the slot on the complementary slice into the slot on the primary slice.

In sum, given a slice plane and a virtual 3D model created by a user, the slicing engine generates two or more slices of the 3D model. The slicing engine then determines connection points on each of the slices that indicate how the 3D model is to be reconnected by the user when the 3D model is fabricated. The slicing engine also determines an optimized layout for the various slices of the 3D model on fabrication material for minimal use of the material. The user is then able to "print" the layout on the fabrication material via 3D printers, and connect the various printed slices according to the connection points to build a physical representation of the 3D model.

One advantage of the disclosed techniques is that an end-user is able to build 3D models quickly and without the need of a professional third party manufacturer. More specifically, the slicing engine processes a virtual 3D model in such a manner that, to physically manufacture the 3D model, a user simply prints the layout of the slices generated by the slicing engine onto fabrication material and then connects the slices to build the model. The mechanism to assemble various manufactured slices of the 3D model is also greatly simplified by the connection points that are identified by the slicing engine per slice. Further, the slicing engine generates assembly instructions that provide a step-by-step guide to the user to assemble the slices of the 3D model.

While the forgoing is directed to embodiments of the present disclosure, other and further embodiments of the disclosure may be devised without departing from the basic scope thereof. For example, aspects of the present disclosure may be implemented in hardware or software or in a combination of hardware and software. One embodiment of the disclosure may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the present disclosure, are embodiments of the present disclosure.

In view of the foregoing, the scope of the present disclosure is determined by the claims that follow.

We claim:

1. A computer-implemented method for generating a real-world three-dimensional (3D) graphics model, the method comprising:
   slicing the 3D graphics model along a primary axis to generate a plurality of primary slices;
   slicing the 3D graphics model along a secondary axis to generate a plurality of secondary slices;
   determining that a first slice included in the plurality of primary slices is to be connected to a second slice included in the plurality of secondary slices;
   identifying a connection location on each of the first slice and the second slice where the first slice and the second slice are to be connected, wherein the connection location is a slot; and
   causing an indication of the connection location to be generated on each of the first slice and the second slice when the first slice and the second slice are manufactured.

2. The method of claim 1, wherein slicing the 3D graphics model comprises determining the primary axis along which the 3D graphics model is to be sliced based on a slice plane.

3. The method of claim 2, wherein slicing the 3D graphics model further comprises determining a width interval on the 3D graphics model at which the first slice is to be generated, and drawing a plane that is orthogonal to the primary axis and intersects the 3D graphics model at the width interval.

4. The method of claim 3, wherein the 3D graphics model comprises a triangulated mesh, and wherein slicing the 3D graphics model further comprises identifying a subset of triangles belonging to the triangulated mesh, wherein each triangle in the subset intersects a plane boundary associated with the plane.

5. The method of claim 4, wherein slicing the 3D graphics model further comprises combining a plurality of line segments included in the subset of triangles to form a slice boundary associated with the first slice, wherein each line segment in the plurality of line segments is included in a different triangle in the subset of triangles and intersects the boundary associated with the plane.

6. The method of claim 1, wherein the secondary axis is orthogonal to the primary axis.

7. The method of claim 1, further comprising generating a layout of the first slice and the second slice on a fabrication material.

8. A non-transitory computer readable medium storing instructions that, when executed by a processor, cause the processor to generate a real-world three-dimensional (3D) graphics model, by performing the steps of:
   slicing the 3D graphics model along a primary axis to generate a plurality of primary slices;
   slicing the 3D graphics model along a secondary axis to generate a plurality of secondary slices;
   determining that a first slice included in the plurality of primary slices is to be connected to a second slice included in the plurality of secondary slices;
   identifying a connection location on each of the first slice and the second slice where the first slice and the second slice are to be, wherein the connection location is a slot; and
   causing an indication of the connection location to be generated on each of the first slice and the second slice when the first slice and the second slice are manufactured.

9. The non-transitory computer readable medium of claim 8, wherein slicing the 3D graphics model comprises determining the primary axis along which the 3D graphics model is to be sliced based on a slice plane.

10. The non-transitory computer readable medium of claim 9, wherein slicing the 3D graphics model further comprises determining a width interval on the 3D graphics model at which the first slice is to be generated, and drawing a plane that is orthogonal to the primary axis and intersects the 3D graphics model at the width interval.

11. The non-transitory computer readable medium of claim 10, wherein the 3D graphics model comprises a triangulated mesh, and wherein slicing the 3D graphics model further comprises identifying a subset of triangles belonging to the triangulated mesh, wherein each triangle in the subset intersects a plane boundary associated with the plane.

12. The non-transitory computer readable medium of claim 11, wherein slicing the 3D graphics model further comprises combining a plurality of line segments included in the subset of triangles to form a slice boundary associated with the first slice, wherein each line segment in the plurality of line segments is included in a different triangle in the subset of triangles and intersects the boundary associated with the plane.

13. The non-transitory computer readable medium of claim 8, wherein the secondary axis is orthogonal to the primary axis.

14. The non-transitory computer readable medium of claim 8, further comprising generating a layout of the first slice and the second slice on a fabrication material.

15. A computer system, comprising:
   a memory; and
   a processor configured to:
      slice a 3D graphics model generated by a software application along a primary axis to generate a plurality of primary slices,
      slice the 3D graphics model along a secondary axis to generate a plurality of secondary slices,
      determine that a first slice included in the plurality of slices is to be connected to a second slice also included in the plurality of slices,
      identify a connection location on each of the first slice and the second slice where the first slice and the second slice are to be connected, wherein the connection location is a slot; and cause an indication of the connection location to be generated on each of the first slice and the second slice when the first slice and the second slice are manufactured.

16. The computer system of claim 15, wherein the processor is configured to determine the primary axis along which the 3D graphics model is to be sliced based on a slice plane.

17. The computer system of claim 16, wherein the processor is configured to determine a width interval on the 3D graphics model at which the first slice is to be generated, and drawing a plane that is orthogonal to the primary axis and intersects the 3D graphics model at the width interval.

18. The computer system of claim 17, wherein the 3D graphics model comprises a triangulated mesh, and wherein slicing the 3D graphics model further comprises identifying a subset of triangles belonging to the triangulated mesh, wherein each triangle in the subset intersects a plane boundary associated with the plane.

* * * * *